United States Patent [19]  [11] 4,162,988
Maze et al. [45] Jul. 31, 1979

[54] BIPHENYL ESTER LIQUID CRYSTAL COMPOUNDS

[75] Inventors: Robert C. Maze; Everett P. Oppenheim, both of Tempe; Reese M. Reynolds, Phoenix, all of Ariz.

[73] Assignee: Motorola, Inc., Schaumburg, Ill.

[21] Appl. No.: 883,623

[22] Filed: Mar. 6, 1978

Related U.S. Application Data

[63] Continuation of Ser. No. 707,479, Jul. 21, 1976, abandoned.

[51] Int. Cl.² .................. C07C 143/68; C09K 3/34
[52] U.S. Cl. .................. 252/299; 260/349; 260/455 R; 260/465 D; 560/19; 560/21; 560/59; 560/102; 560/107
[58] Field of Search .................. 260/455 R; 252/299

[56] References Cited

U.S. PATENT DOCUMENTS 3,947,375 3/1976 Gray et al. .................. 252/299
4,065,489 12/1977 Steinsträsser et al. .................. 252/299 X Primary Examiner—Dolph H. Torrence
Attorney, Agent, or Firm—John A. Fisher

[57] ABSTRACT

Novel compounds exhibiting liquid crystal properties have the formula:

R-φ-φ-X-φ-R1, wherein
R and R1 are, independently in each case, hydrogen or an alkyl, aryl, alkylaryl, arylalkyl, or alkoxy group containing from 1 to about 12 carbon atoms, a halogen, a cyano group, an alkyl cyano group of from 1 to 5 carbon atoms, a —CF₃ group, an —N₃ group, a nitro group or a —N(CH₃)₂ group, and
X is

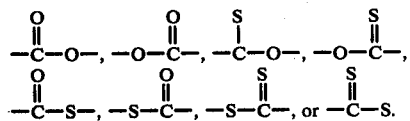

These compounds are especially useful for increasing the clearing point and reducing the operating voltage of liquid crystal compositions including other ester or Schiff base liquid crystal compounds, and the like.

2 Claims, No Drawings

BIPHENYL ESTER LIQUID CRYSTAL COMPOUNDS

This is a continuation of application Ser. No. 707,479, filed July 21, 1976 and now abandoned.

BACKGROUND OF THE INVENTION

1. Field of the Invention

This invention relates to a new class of ester or ester liquid crystal compounds. More particularly, it relates to esters and sulfur esters having a biphenyl moiety and which exhibit liquid crystal properties.

2. Description of the Prior Art

Various liquid crystal compositions have been disclosed in the prior art. A typical desired specification for a field effect nematic liquid crystal display composition includes a temperature range of from about 0° to about 60° C., with the lower temperature indicating the melting point of the material and the upper temperature indicating the clearing or nematic isotropic temperature. Second, a threshold voltage of from about 1.0 to about 1.5 volts and an operating voltage of from about 1.5 volts to about 2.5 volts is desired. Third, the composition should exhibit sufficient optical contrast for display purposes when incorporated in a liquid crystal display structure. Fourth, the lifetime of the liquid crystal composition should be at least about five years. Fifth, the resistivity of the composition should be at least about $5 \times 10^9$ ohm centimeters.

Various ester liquid crystal compounds are known in the art, such as the phenylbenzoate esters described in U.S. Pat. No. 3,876,286. While such compounds are known to be highly stable, they generally have higher melting points and narrower nematic temperature ranges than other types of liquid crystal compounds, such as Schiff bases. Broadening of the operating temperature range for ester liquid crystal compounds may be achieved by preparing a blend of different esters, each contributing a characteristic feature to the overall composition. In order to meet the needs of the rapidly developing, highly competitive liquid crystal technology, there remains a requirement for new compounds that may be used to tailor liquid crystal compositions with desired properties, particularly for increased clearing points and reduced operating voltages.

SUMMARY OF THE INVENTION

Accordingly, it is an object of this invention to provide an ester or sulfur ester liquid crystal compound useful for increasing the clearing point of liquid crystal mixtures.

It is another object of this invention to provide an ester or sulfur ester liquid crystal compound suitable for reducing the operating voltage of liquid crystal mixtures.

It is still another object of the invention to provide an ester or sulfur ester liquid crystal compound which will increase the clearing point and reduce the operating voltage of ester or sulfur ester liquid crystal mixtures, and which is compatible in admixture with other liquid crystal compounds known in the art.

The attainment of these and related objects may be achieved through use of the novel ester or sulfur ester liquid crystal compounds containing a biphenyl moiety herein disclosed.

The biphenyl moiety containing liquid crystal esters or sulfur esters in accordance with this invention have the formula:

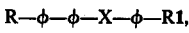

wherein

R and R1 are, independently in each case, hydrogen or an alkyl, aryl, alkylaryl, arylalkyl or alkoxy group containing from 1 to about 12 carbon atoms, a halogen, a cyano group, an alkyl cyano group of from 1 to 5 carbon atoms, a —CF$_3$ group, an —N$_3$ group, a nitro group or a —N(CH$_3$)$_2$ groups, and X is

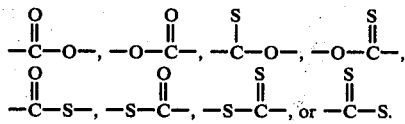

As used herein, the symbol φ represents a benzene ring in which the hydrogen atoms at other than the para ring position may be replaced by inert substituents, such as halogen atoms or an alkyl group of from 1 to 5 carbon atoms, or the like. Preferred compounds in accordance with the invention have the above structural formula, in which R and R1 are each hydrogen, have from four to seven carbon atoms, or are a cyano or nitro group. In these especially preferred compounds, X is:

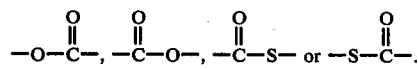

Compounds having the above general formula can be prepared by methods known in the art for the preparation of ester and sulfur ester liquid crystal compounds. For example, they may be prepared by reaction of acyl chloride with a substituted phenol, as employed in the art to prepare phenylbenzoate esters. Further details of this preparation technique may be found in the above referenced U.S. Pat. No. 3,876,286, the disclosure of which is hereby incorporated by reference herein.

The compounds of this invention may be mixed with other chemically compatible liquid crystal compounds to provide an overall composition with the desired operating characteristics. In particular, the compounds of this invention are ideally suited for mixing with other phenylbenzoate esters or sulfur esters, and Schiff bases.

With respect to the amounts of the individual compounds employed in the compositions of this invention, it is preferred to prepare substantially eutectic mixtures. By the term "substantially eutectic" in this application is meant a mixture wherein each component thereof is present within a value of about 5% of its amounts in the system that will give the lowest melting point for the mixture. Thus, if a compound has a eutectic proportion of 10 weight percent it could be present between about 5 and 15 weight percent within the meaning of this term. In general, it has been found that the ester or sulfur ester liquid crystal compositions in accordance with this invention require at least about 1 mole percent of the novel biphenyl moiety containing liquid crystal compounds of this invention in order for these biphenyl moiety containing compounds to have a measurable impact on the clearing point and operating voltages of the compositions. In general, the addition of about 1 mole percent of the compounds of this invention will increase the clearing point of a phenylbenzoate ester liquid crystal mixture by about 1.8° C.

The compounds and compositions of this invention are particularly useful in a twisted nematic, field effect liquid crystal display for such applications as electronic wristwatches, electronic calculators, digital volt meters and the like. Such twisted mematic, field effect liquid crystal displays are well known in the art.

The following nonlimiting examples will serve to illustrate the practice of this invention and represent best modes contemplated by the inventor of the invention.

EXAMPLE I

A series of compounds in accordance with the general formula given above, having X, R and R1 as indicated in the table below were prepared by the following generalized procedure. A substituted benzoyl chloride is added in a stoichiometric quantity to a substituted phenol (or thiophenol in the case of a sulfur ester), dissolved in an inert solvent, such as bezene or toluene. To this is added a nucleophilic scavenging agent, such as pyridine or triethylamine, also in stoichiometric amount, to trap out hydrochloric acid released in the reaction. The reaction is carried out at a temperature between room temperature and the boiling point of the solvent employed for a time from about one hour to about 15 hours. The reaction product is then purified by conventional techniques, such as solvent-solvent extractions, including weak acid and weak base extractions. If such techniques do not produce sufficient purity of the desired compound, further purification is carried out with hexamethyl-disilazane (HMDS), as more fully set out below, and as disclosed in the digest of papers for the 1975 Pacific Conference on Chemistry and Spectroscopy, North Hollywood, Calif., Oct. 28-30, 1975, page 90.

For example, to prepare the first compound set out in the table below, biphenyl carbonyl chloride is added as a solid to a stoichiometric equivalent of 4-cyanophenol, previously dissolved in benzene. To the above, a stoichiometric equivalent of triethylamine is added and the resulting mixture is stirred at reflux temperature for from 4 to 12 hours. At the end of this time, the reaction product is diluted by washing into a separatory funnel with benzene, washing twice with water, twice with 5% by weight hydrochloric acid, twice with water, three times with saturated sodium bicarbonate solution, and twice with water. The organic phase is then dried over a dessicating agent, such as molecular sieves. The organic solvent is removed by evaporation and the residual product is recrystallized twice in a suitable solvent system, for example, a mixture of ethyl acetate and petroleum ether (LeGroin). If the ester product is not 99% or more pure, it is repurified with HMDS as follows: the product is dissolved in an aprotic solvent, such as benzene or ethyl acetate. A two times equivalent amount of HMDS is added, and the solution is allowed to stir at room temperature for from 2-12 hours. The aprotic solvent is removed by evaporation under reduced pressure and any protic impurities which are now volatilized by silylation with the HMDS are removed by placing the sample under vacuum at about 50 microns of mercury pressure for from 2-4 hours. The product is recrystallized at least once in a suitable solvent, typically the ethyl acetate-petroleum ether mixture.

To reverse the ester group in the first compound in the table, a substituted benzoyl chloride and a 4-substituted phenol replaces the initial reagents, and the same procedure as set out above is utilized.

| X | R | R1 | MELTING POINT | CLEARING POINT |
|---|---|---|---|---|
| $-\overset{O}{\underset{\|\|}{C}}-O-$ | H | CN | 154.8 | 180.4° |
| $-O-\overset{O}{\underset{\|\|}{C}}-$ | n-$C_5H_{11}O-$ | H | 148.3 | 116 |
| $-O-\overset{O}{\underset{\|\|}{C}}-$ | n-$C_4H_9O-$ | H | 67.2 | 60.4 |
| $-\overset{O}{\underset{\|\|}{C}}-O-$ | H | $\phi$ | 224 | 209 |
| $-\overset{O}{\underset{\|\|}{C}}-O-$ | H | $-NO_2$ | 162 | 178 |
| $-\overset{O}{\underset{\|\|}{C}}-S-$ | H | $-NO_2$ | 184 | 193 |

Each of the compounds in the table exhibited liquid crystal properties, having the melting points and clearing points indicated for each compound in the table. In general, the clearing points obtained for these compounds indicate that esters and sulfur esters having a biphenyl moiety and exhibiting liquid crystal properties tend to have higher clearing points than similar compounds which lack the biphenyl moiety. This example further shows that both ester and sulfur ester compounds containing the biphenyl moiety exhibit liquid crystal properties.

EXAMPLE II

Liquid crystal compositions including compounds in accordance with this invention are prepared by admixture of the liquid crystal compounds in the amounts shown in the following tables. In each case, parallel compositions are prepared not including a compound of this invention for comparative pruposes. The tables also show the melting point and clearing point of each composition.

EXAMPLE II-A

| | WEIGHT FRACTION | |
|---|---|---|
| I $C_2H_5$ $\phi$-$CO_2$-$\phi CN$ | .161 | .164 |
| II $C_4H_9$ $\phi$-$CO_2$-$\phi CN$ | .172 | .175 |
| III $C_5H_{11}$ $\phi$-$CO_2$-$\phi CN$ | .129 | .131 |
| IV $C_5H_{11}$ $\phi$-$\phi$-CN | .522 | .530 |

EXAMPLE II-B

| | WEIGHT FRACTION | |
|---|---|---|
| I $CH_3O$ $\phi$-$CO_2$-$\phi C_5H_{11}$ | .465 | .473 |
| II $C_2H_5$ $\phi$-$CO_2$-$\phi CN$ | .177 | .180 |
| III $C_4H_9$ $\phi$-$CO_2$-$\phi CN$ | .194 | .198 |
| IV $C_5H_{11}$ $\phi$-$CO_2$-$\phi CN$ | .147 | .150 |
| V $\phi$-$\phi$-$CO_2$-$\phi CN$ | .018 | — |
| Melting Point | 1.8° C. | 2.3 |
| Clearing Point | 48.2° C. | 45.9 |

These liquid crystal compositions show that small amounts of the biphenyl moiety containing liquid crystal compounds will increase the clearing point of liquid crystal compositions substantially. Larger amounts of these compounds will increase the clearing point a proportionate amount. It should further be noted that these compounds do not increase the melting point of the compositions substantially. This means that the increase in clearing point serves to extend the operating range of the compositions in accordance with the invention.

It should now be apparent that compounds and compositions capable of achieving the stated objects of the invention have been provided. The compounds of this invention serve to enhance the properties of liquid crystal mixture including them. Further, the compounds are chemically compatible with other liquid crystal mixtures.

It should further be apparent to the art skilled that various changes in form and detail in this invention can be made. It is intended that such changes be included within the spirit and scope of the claims appended hereto.

What is claimed is:

1. A compound having the formula

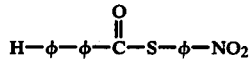

wherein $\phi$ represents a benzene ring and wherein the designated groups are substituted at the para ring position.

2. An improved liquid crystal composition comprising a substantially eutectic mixture of two or more phenylbenzoate ester liquid crystal compounds selected from the group consisting of $C_2H_5-\phi-CO_2-\phi-CN$, $C_4H_9-\phi-CO_2-\phi-CN$, $C_5H_{11}-\phi-CO_2-\phi-CN$, and $CH_3O-\phi-CO_2-\phi-C_5H_{11}$, wherein the improvement comprises the addition to said mixture of a compound having the formula of claim 1.

* * * * *